United States Patent [19]

Isogai et al.

[11] 4,339,597

[45] Jul. 13, 1982

[54] PROCESS FOR PRODUCING 2-PENTENOIC ESTERS

[75] Inventors: Nobuo Isogai; Motoyuki Hosokawa; Takashi Okawa; Natsuko Wakui; Toshiyasu Watanabe, all of Niigata, Japan

[73] Assignee: Mitsubishi Gas Chemical Company, Inc., Tokyo, Japan

[21] Appl. No.: 240,966

[22] Filed: Mar. 5, 1981

[30] Foreign Application Priority Data

Mar. 24, 1980 [JP] Japan ................................. 55/37128

[51] Int. Cl.$^3$ .......................................... C07C 67/333
[52] U.S. Cl. .................................... 560/205; 252/463
[58] Field of Search ........................................ 560/205

[56] References Cited

U.S. PATENT DOCUMENTS 4,036,904  7/1977  Strope .................................. 585/370

OTHER PUBLICATIONS

Rhoades, Sara Jane et al., "Double-Bond Isomerization in Unsaturated Esters and Enol Ethers", *J. Org. Chem.*, vol. 35, (1970), pp. 3352-3358.

Leach, Bruce E., *Chemical Abstracts*, vol. 84, (1976), #80,366w.

*Primary Examiner*—Natalie Trousof
*Assistant Examiner*—L. Hendriksen
*Attorney, Agent, or Firm*—Fleit & Jacobson

[57] ABSTRACT

A process for producing a 2-pentenoic ester which comprises contacting the corresponding 3-pentenoic ester with a composite catalyst composed of magnesia and alumina is disclosed.

8 Claims, No Drawings 4,339,597

PROCESS FOR PRODUCING 2-PENTENOIC ESTERS

BACKGROUND OF THE INVENTION

This invention relates to a process for producing a 2-pentenoic ester which comprises isomerizing the corresponding 3-pentenoic ester.

In general, many prior processes for isomerizing unsaturated carboxylates are known. For example, (a) J. Chem. Soc. 2454 (1957) discloses a process for isomerizing a 3-hexenoic ester in the presence of potassium hydroxide as a catalyst; (b) J. Org. Chem. 35 3352 (1970) discloses a process for isomerizing methyl 3-pentenoate in the presence of sodium methylate or iron pentacarbonyl; and (c) Bull. Chem. Soc. Jpn., 51 2970 (1978) discloses a process for isomerizing dimethyl methylenesuccinate to dimethyl 2-methylbutenoate in the presence of triethylamine.

However, in process (a), the esters employed as a raw material and isomerized are hydrolyzed by the alkali hydroxide to form the alkali salt of unsaturated carboxylic acids. In order to avoid this shortcoming, the alkali salt of unsaturated carboxylic acid should be neutrilized and esterified. This is complicated.

In process (b) in which sodium methylate is used, sodium methylate adds to the double bond of the unsaturated carboxylate. This lowers the yield of 2-pentenoic ester. In process (b) in which iron pentacarbonyl is used, the reaction speed is slow and, also, the reaction is necessarily effected under an atmosphere pressurized by carbon monoxide, because iron pentacarbonyl is unstable.

In process (c), isomerization of dimethyl methylenesuccinate to dimethyl 2-methylbutenoate proceeds in the presence of triethylamine even at room temperature, and little side reaction occurs. However, isomerization reaction of a 3-pentenoic ester to the corresponding 2-pentenoic ester in the presence of triethylamine slowly proceeds even at 100° C. This is too slow to be industrially practicable.

In addition, these known processes are effected in a liquid phase homogeneous reaction. In this case, an apparatus for separating the catalysts from the resulting reaction mixtures is necessary. This makes the process unsatisfactory from an industrial point of view.

SUMMARY OF THE INVENTION

The inventors of this invention carried out research for overcoming the shortcomings of the prior art. As a result, we found that when a 3-pentenoic ester contacts a composite catalyst composed of magnesia and alumina, the corresponding 2-pentenoic ester can be formed in a high yield at excellent reaction speed and without causing any substantial side reaction.

An object of this invention is to provide a process for producing a 2-pentenoic ester from the corresponding 3-pentenoic ester in a high yield at fast reaction speed and without causing any substantial undesirable side reaction.

DETAILED DESCRIPTION OF THE INVENTION

The composite catalyst composed of magnesia and alumina employed in the practice of this invention can be prepared by the following conventional methods: (a) at least one of magnesium oxide, magnesium hydroxide and magnesium carbonate and at least one of aluminum oxide, aluminum hydroxide and aluminum salts of organic acids are blended. Water enough to form a paste is added to the mixture to form paste. The paste is blended and kneaded, and then baked in air or in an inert gas to obtain a composite catalyst composed of magnesia and alumina; and (b) the precipitate obtained by coprecipitating mixture of a magnesium salt and an aluminum salt with an alkaline substance, such as ammonium carbonate, sodium carbonate or sodium hydroxide is baked in air or an inert gas to obtain a composite catalyst composed of magnesia and alumina.

The baking temperature may be in the range of 350° C. to 800° C., preferably 400° C. to 650° C.

The molar ratio of magnesia to alumina in the catalyst can vary over the wide range. In general, the molar ratio of magnesia to alumina may be in the range of 1:100 to 100:1, preferably 1:20 to 20:1.

The isomerization reaction temperature is not critical. The temperature may range from 50° C. to 300° C., preferably 80° C.–250° C. Though the reaction proceeds at a temperature below 50° C., this is not preferable because of the slower reaction speed. On the other hand, a temperature higher than 300° C. is likely to cause side reactions.

According to the present invention, methyl 2-pentenoate and ethyl 2-pentenoate can be produced from the corresponding 3-pentenoic esters. Other 2-pentenoic esters can also be produced.

The reaction pressure may be effected under reduced pressure, atmospheric pressure or superpressure.

The present process can be effected in a gas phase catalytic reaction or a liquid phase catalytic reaction.

In other words, the present process can be effected in a gas phase catalytic reaction under the following conditions:

(a) at a temperature above the boiling point of the 3-pentenoic ester employed as a raw material;

(b) under reduced pressure; or (c) in the presence of a inert gas, such as a nitrogen gas.

Alternatively, the present process can be effected in a liquid phase catalytic reaction under the following conditions:

(a) at a temperature below the boiling point of the 3-pentenoic ester employed as a raw material;

(b) under superpressure; or (c) at a temperature higher than the boiling point of the 3-pentenoic ester employed as a raw material provided that a solvent having a boiling point higher than that of the 3-pentenoic ester is used.

When the reaction is effected in the presence of an inert gas, concentration of a 3-pentenoic ester can vary over the wide range. In general, the concentration of a 3-pentenoic ester may be in the range of 1–99% by mol. Too low concentration of a 3-pentenoic ester is not preferable from economical point of view.

The isomerization reaction may be effected without any solvent or in the presence of at least one solvent. The solvents employed in the practice of this invention include, for example, aliphatic hydrocarbons such as hexane; aromatic hydrocarbons such as toluene; ethers, such as diethyl ether or dioxane; amides, such as N-methyl-2-pyrrolidone or hexamethyl phosphoric triamide; nitrile, such as acetonitrile; ketones, such as acetone; tertiary amines, such as triethylamine, pyridine or quinoline; organic acid ester, such as ethyl acetate;

dialkylsulfoxide, such as dimethylsulfoxide; or sulforane.

When a solvent having a low boiling point is used, the reaction can be effected in a liquid phase catalytic reaction under superpressure within a certain temperature range.

When the isomerization reaction is effected in a liquid phase catalytic reaction in the presence of a solvent, the concentration of the 3-pentenoic ester may be in the range of 1-99% by mol, preferably 5-80% by mol.

Space velocity in a gas phase catalytic reaction depends on the concentration of the 3-pentenoic ester and the reaction temperature. In general the space velocity may be in the range of 1-10,000 $hr^{-1}$, preferably 50-4000 $hr^{-1}$.

Liquid space velocity in a liquid phase catalytic reaction also depends on the concentration of the 3-pentenoic ester and the reaction temperature. In general the liquid space velocity may be in the range of 0.01-10 $hr^{-1}$, preferably 0.05-5 $hr^{-1}$.

According to this invention a 3-pentenoic ester can be isomerized to the corresponding 2-pentenoic ester without causing substantial any side reaction in a high yield. Since the present process can be effected in a catalytic reaction, a special apparatus for separating the catalyst employed is not necessary.

This invention is illustrated by the following Examples. This invention should not be limited by the Examples. The yields given in these Examples are all the ones obtained without recirculating methyl 3- and 4-pentenoate left in the reaction system after recovering methyl 2-pentenoate (one pass yield). In practice, the yield becomes better, since the methyl 3- and 4-pentenoate are usually recirculated into the isomerization zone for further isomerization reaction.

PREPARATION 1 OF CATALYST

An aqueous solution of magnesium nitrate (0.6 mol/l), an aqueous solution of aluminum nitrate (0.2 mol/l), an aqueous solution of sodium carbonate (0.1 mol/l) and an aqueous solution of sodium hydroxide (0.2 mol/l) were charged continuously at different streams at room temperature with stirring. The feeding speed of the aqueous solution of sodium hydroxide was adjusted to that pH of the reactants was maintained within the range of 10-11. The molar ratio of magnesia to alumina can be adjusted by varying the feeding speed each of the aqueous solution of magnesium nitrate and the aqueous solution of aluminum nitrate. The resulting slurry was filtered, washed with water and dried at 100° C. for 10 hours. The resulting solid was crushed to particles of 6-10 mesh. The particles were baked in air at 500° C. for 2 hours to obtain the catalyst employed in the practice of this invention.

The reactor employed in the following Examples was a pyrex glass pipe having inside diameter of 20 mm and length of 700 mm. The reactor can be heated in an electric furnace.

Rasching rings of 10 ml were placed over the catalyst layer. The raw material was preheated in the layer of Rasching rings.

EXAMPLE 1

15 ml of catalyst of composed magnesia and alumina (molar ratio of 6:1) was placed in the reactor. The layer of catalyst was maintained at 180° C. by heating the reactor. Methyl 3-pentenoate was dropwise added to the reactor from the upper portion of the reactor at feeding speed of 10 g/hr to cause isomerization reaction. A gas phase catalytic reaction was effected. The space velocity was 130 $hr^{-1}$. The resulting product gas was cooled by cooling means to collect liquid product.

The yield of methyl 2-pentenoate was 50.6 mol % and the yield of methyl 4-pentenoate was 2.4 mol %. The product contained unreacted methyl 3-pentenoate of 46.9 mol %. Substantially no other by-product was present.

EXAMPLE 2

Catalyst (15 ml) composed of magnesia and alumina (molar ratio of 6:1) was charged into the reactor. The layer of catalyst was heated to 120° C. while flowing nitrogen gas at flow speed of 12 l/hr. At that temperature methyl 3-pentenoate was dropwise added to the reactor from the upper portion of the reactor at feeding speed of 2 g/hr to cause a gas phase catalytic reaction. The space velocity was 826 $hr^{-1}$. The resulting product gas was introduced into a solution of acetone cooled in ice-water bath and the product was absorbed in the acetone solution. Thereafter, the nitrogen gas was removed. The yield of methyl 2-pentenoate was 57.4 mol %. The yield of methyl 4-pentenoate was 3.8 mol %. The product contained unreacted methyl 3-pentenoate of 38.7 mol %. Substantial no other by-product was present.

EXAMPLE 3

Catalyst (15 ml) composed of magnesia and alumina (molar ratio of 20:1) was charged into the reactor. The layer of catalyst was heated to 150° C. while flowing a nitrogen gas at flow speed of 20 l/hr. At that temperature methyl 3-pentenoate was dropwise added to the reactor from the upper portion of the reactor at feeding speed of 3 g/hr to cause a gas phase catalytic reaction. The space velocity was 1370 $hr-1$. The resulting product gas was introduced into a solution of acetone cooled in ice-water bath and the product was absorbed in the acetone solution. Thereafter, then the nitrogen gas was removed. The yield of methyl 2-pentenoate was 55.0 mol %. The yield of methyl 4-pentenoate was 3.1 mol %. The product contained unreacted methyl 3-pentenoate of 41.81 mol %. Substantial no other by-product was present.

EXAMPLE 4

Catalyst (15 ml) composed of magnesia and alumina (molar ratio of 6:1) was charged into the reactor. The layer of catalyst was heated to 100° C. Methyl 3-pentenoate was dropwise added to the reactor from the upper portion of the reactor at feeding speed of 2 g/hr to cause a liquid phase catalytic reaction. The liquid space velocity was 0.12 $hr^{-1}$. The yield of methyl 2-pentenoate was 40.2 mol %. The yield of methyl 4-pentenoate was 1.3 mol %. The product contained unreacted methyl 3-pentenoate of 58.4 mol %. Substantial no other by-product was present.

EXAMPLE 5

The procedure of Example 4 was repeated except that the reaction temperature was 150° C., and a mixture of 10 wt% of methyl 3-pentenoate and 90 wt% of dimethyl sulfoxide was charged to the reactor at feeding speed of 15 g/hr. In this case a liquid phase catalytic reaction was effected. The liquid space velocity was 1.1 $hr^{-1}$. The yield of methyl 2-pentenoate was 48.3 mol % and the yield of methyl 4-pentenoate was 2.1 mol %.

The product contained unreacted methyl 3-pentenoate of 49.5 mol %. Substantial no other by-product was present.

EXAMPLE 6

The procedure of Example 3 was repeated except that catalyst composed of magnesia and alumina (molar ratio of 1:2) was used, and the reaction temperature was 200° C. The yield of methyl 2-pentenoate was 36.5 mol % and the yield of methyl 4-pentenoate was 1.8 mol %. The product contained unreacted methyl 3-pentenoate of 61.5 mol %. Substantial no other by-product was present.

What is claimed is:

1. A process for producing a 2-pentenoic ester which comprises contacting the corresponding 3-pentenoic ester with a composite catalyst composed of magnesia and alumina to isomerize the 3-pentenoic ester.

2. The process as defined in claim 1 wherein the isomerization is effected in a gas phase catalytic reaction.

3. The process as defined in claim 1 wherein the isomerization is effected in a liquid phase catalytic reaction.

4. The process as defined in claim 1 wherein the molar ratio of magnesia to alumina in the catalyst is in the range of 1:100 to 100:1.

5. The process as defined in claim 4 wherein the molar ratio of magnesia to alumina in the catalyst is in the range of 1:20 to 20:1.

6. The process as defined in claim 2 wherein the space velocity is in the range of 1–10,000 $hr^{-1}$.

7. The process as defined in claim 3 wherein the liquid space velocity is in the range of 0.01–10 $hr^{-1}$.

8. The process as defined in claim 1 wherein the isomerization is effected at a temperature in the range of 50° C.–300° C.

* * * * *